United States Patent [19]

Lee

[11] Patent Number: 5,225,571
[45] Date of Patent: Jul. 6, 1993

[54] SUBSTITUTED DIHYDROXY-BIS-[5-HYDROXY-2(5H)-FURANONE-4-YL]-ALKANES AS ANTI-INFLAMMATORY AGENTS

[75] Inventor: Gary C. M. Lee, Laguna Hills, Calif.
[73] Assignee: Allergan, Inc., Irvine, Calif.
[21] Appl. No.: 693,201
[22] Filed: Apr. 30, 1991
[51] Int. Cl.$^5$ .............. C07F 9/06; C07F 9/28; C07D 307/60
[52] U.S. Cl. .................. 549/222; 549/313
[58] Field of Search .............. 514/99, 471, 473; 549/313, 222

[56] References Cited

U.S. PATENT DOCUMENTS

| | | | |
|---|---|---|---|
| 2,359,096 | 9/1944 | Elderfield | 260/239.5 |
| 2,359,208 | 9/1944 | Elderfield | 260/344 |
| 4,447,445 | 5/1984 | Jacobs | 424/279 |
| 4,786,651 | 11/1988 | Wheeler | 514/460 |
| 4,789,749 | 12/1988 | Jacobs et al. | 549/313 |
| 4,855,320 | 8/1989 | Chatterjee et al. | 514/473 |
| 4,874,782 | 10/1989 | Bonjouklian et al. | 514/473 |
| 4,916,241 | 4/1990 | Hayward et al. | 549/313 |
| 4,935,530 | 6/1990 | Lee | 549/214 |
| 5,013,850 | 5/1991 | Lee | 549/222 |
| 5,037,811 | 8/1991 | Lee | 514/99 |
| 5,043,457 | 8/1991 | Lee | 549/222 |
| 5,045,564 | 9/1991 | Lee | 514/471 |

FOREIGN PATENT DOCUMENTS

| | | |
|---|---|---|
| 133376 | 2/1985 | European Pat. Off. . |
| 209274 | 1/1987 | European Pat. Off. . |
| 295056 | 6/1987 | European Pat. Off. . |
| 350878 | 1/1990 | European Pat. Off. . |

OTHER PUBLICATIONS

Bonjuklian, et al., Chemical Abstracts, vol. 106, 156260c, p. 670 (1987).
Reynolds, et al., J. Am. Chem. Soc., 110, pp. 5172-5177 (1988).
Tocanne et al., Chemical Abstracts 69 76581k, p. 7146 (1968).
Deems, et al., Biochimica et Biophysica Acta, 917, pp. 258-268 (1987).
Scheuer et al., Journal of the American Chemical Society 100:1 p. 307 (Jan. 4, 1978).
Graziano, et al., Chemical Abstracts 107, (1987), 236559t.
Roll et al., Org. Chem. 1988, 53 3276-8.
Negishi et al., J. Org. Chem 45, pp. 5223-5225, (1980).
E. D. de Silva et al., "Tetrahedron Letters", 21:1611-1614 (1980).
Nakagawa et al., "Aldose reductase inhibitor from Palaun sponges" Chem. Abstract 106: 96126b.
Tanaka et al., The Chemical Society of Japan, Chemistry Letters, pp. 633-636 (1983).
Tanis, e al., Tetrahedron Letters, vol. 25, No. 40, pp. 4451-4454 (1984)—Furans in Synthesis 4. Silyl Furans as Butenolide Equivalents.
David Nettleton, et al, Inflammation Research Association, Fifth International Conference Poster Session, Phospholipase A$_2$ Inhibition by Dihydrofuranones, Sep. 23-27, 1990.

Primary Examiner—C. Warren Ivy
Assistant Examiner—A. A. Owens
Attorney, Agent, or Firm—Gabor L. Szekeres; Martin A. Voet; Robert J. Baran

[57] ABSTRACT

Compounds of the formula

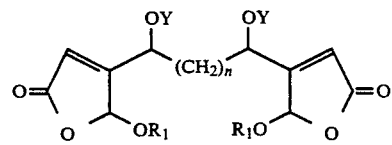

in which R$_1$ is H or alkyl of 1 to 20 carbons, CO—R$_2$, CO—O—R$_2$, CO—NH—R$_2$, or PO(OR$_2$)$_2$ or PO(OR$_2$)R$_2$, where R$_2$ independently is H, alkyl of 1 to 20 carbons, phenyl, or lower alkyl substituted phenyl or halogen substituted phenyl; n is an integer between 8 to 14; Y is H, alkyl having 1-20 carbon atoms, aryl[lower alkyl], aryl, lower alkyl[aryl], alkenyl containing one or more olephinic bonds and 1-20 carbon atoms, CO—R$_3$, CO—OR$_3$, CONHR$_3$, SO$_2$R$_3$, SO$_2$NHR$_3$ where R$_3$ is aryl[lower alkyl], aryl, lower alkyl[aryl], alkenyl containing one or more olephinic bonds and 1-20 carbon atoms, further Y is PO(OH)$_2$, PO(OH)OR$_4$, PO(OH)R$_4$ PO(OR$_4$)$_2$, where R$_4$ is independently alkyl of 1-20 carbons or phenyl, have anti-inflammatory activity.

21 Claims, No Drawings

SUBSTITUTED DIHYDROXY-BIS-[5-HYDROXY-2(5H)-FURANONE-4-YL]-ALKANES AS ANTI-INFLAMMATORY AGENTS

BACKGROUND OF THE INVENTION

1. Field of the Invention

The present invention is directed to novel substituted dihydroxy-bis-[5-hydroxy-2(5H)-furanone-4-yl]-alkanes which are active as anti-inflammatory agents. The present invention is also directed to pharmaceutical compositions which comprise one or more of the novel compounds of the invention, to the methods of using these pharmaceutical compositions, and to the chemical processes of making the novel compounds.

2. Brief Description of the Prior Art

Manoalide is a compound isolated from a marine sponge [E. D. de Silva et al., Tetrahedron Letters 21:1611–1614 (1980)] which has anti-inflammatory, immunosuppressive and analgesic properties. Manoalide the structure of which is shown below, includes a 5-hydroxy-2(5H)-furanone moiety, attached in the 4-position of the furanone ring to the rest of the molecule. Certain analogs of manolide, such as seco-manoalide and dehydro-seco-manoalide also have anti-inflammatory activity. For further description of the biological activity of manoalide and some of its derivatives reference is made to U.S. Pat. Nos. 4,447,445, 4,786,651, 4,789,749 and to European Patent Application No. 0 133 376 (published on Feb. 20, 1985).

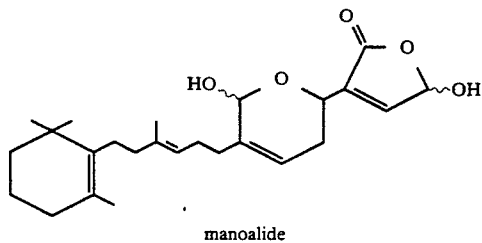

manoalide

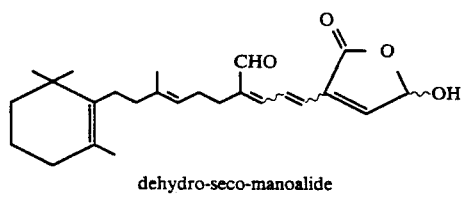

dehydro-seco-manoalide

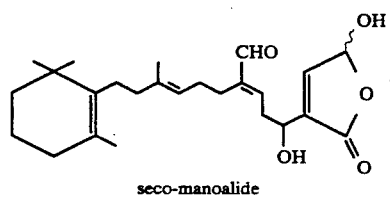

seco-manoalide

Synthetic analogs of manoalide, particularly analogs having various substituents on the furanone moiety of manoalide, are described in several applications for U.S. Pat. by the same inventor as in the present application, the following of which have been allowed and are expected to issue as U.S. Pat.:

Ser. No. 259,225 filed on Oct. 18, 1988 issued as U.S. Pat. No. 4,935,530;

Ser. No. 281,126 filed on Dec. 7, 1988, now abandoned.

Published European Patent Application No. 0 295 056 discloses 4-substituted 5-hydroxy-2(5H)-furanones having anti-inflammatory, immunosuppressive and antiproliferative activity where the substituents in the 4 position are a variety 1-hydroxyalkyl, 1-acyloxy-alkyl and 1-carbamoyloxy-alkyl groups.

U.S. Pat. No. 4,855,320 discloses 5-arylalkyl-4-alkoxy-2(5H)-furanones as anti-convulsive and antiepileptic agents.

Published European Patent Application No. 0 209 274 discloses 4-alkyl-5-hydroxy-2(5H)-furanones as anti-inflammatory and anti-allergy agents.

Chemical Abstracts Volume 107 236559t (1987) discloses 4-acyloxy 5-hydroxy-2(5H)-furanones.

SUMMARY OF THE INVENTION

The present invention covers compounds of Formula 1,

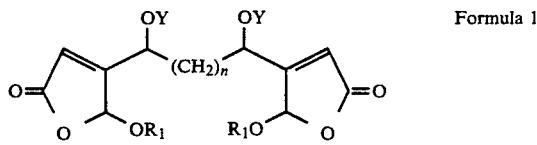

Formula 1 in which $R_1$ is H or alkyl of 1 to 20 carbons, $CO-R_2$, $CO-O-R_2$, $CO-NH-R_2$, or $PO(OR_2)_2$ or $PO(OR_2)R_2$, where $R_2$ independently is H, alkyl of 1 to 20 carbons, phenyl, or lower alkyl substituted phenyl or halogen substituted phenyl;

n is an integer between 8 to 14;

Y is H, alkyl having 1–20 carbon atoms, aryl[lower alkyl], aryl, lower alkyl[aryl], alkenyl containing one or more olefinic bonds and 1–20 carbon atoms, $CO-R_3$, $CO-OR_3$, $CONHR_3$, $SO_2R_3$, $SO_2NHR_3$ where $R_3$ is aryl[lower alkyl], aryl, lower alkyl[aryl], alkenyl containing one or more olefinic bonds and 1–20 carbon atoms, further Y is $PO(OH)_2$, $PO(OH)OR_4$, $PO(OH)R_4$ $PO(OR_4)_2$, where $R_4$ is independently alkyl of 1–20 carbons or phenyl.

The present invention also covers salts of the above-defined compounds, formed with pharmaceutically acceptable acids or bases, as applicable.

In a second aspect, the present invention relates to pharmaceutical formulations comprising one or more compounds of Formula 1 (or pharmaceutically acceptable salts thereof) in admixture with a pharmaceutically acceptable excipient, for the purpose of treating certain conditions, syndromes or diseases in mammals, including humans. The compounds of the invention have anti-inflammatory, immunosuppressant and anti-proliferative activity. Therefore, the compounds are useful for treating in mammals (including humans) inflammation, psoriasis, rheumatoid arthritis, osteoarthritis, rheumatic carditis, ocular and dermal inflammatory diseases, autoimmune diseases such as allergic diseases, bronchial asthma and myasthenia gravis, and for suppressing unwanted immune responses and retarding proliferation of cell.

In still another aspect, the present invention relates to the processes of making the compounds of Formula 1. In general terms, these processes, shown in a summarized fashion in Reaction Scheme 1 comprise the steps of reacting a 2-trialkylsilyl-4-furaldehyde (Formula 2)

with a Grignard (or like) reagent of Formula 3 where X is chlorine, bromine or iodine. The Grignard reagent is derived from a dihalo alkane of the formula X—(CH$_2$)$_n$—X where n is defined as in connection with Formula 1. As a result of the Grignard reaction, the alpha, omega dihydroxy -bis-[2-trialkylsilyl-4-furyl]-alkanes of Formula 4 are obtained. The compounds of Formula 4 are exposed to singlet oxygen to provide compounds of Formula 5. The compounds of Formula 5 are compounds of the invention, where, with reference to Formula 1, Y is H, and R$_1$ is H.

detail and is specifically illustrated in the appended examples, reaction of the herein-described furane derivatives with singlet oxygen involves irradiation of the furane derivatives in the presence of oxygen in a suitable solvent.

The compounds of Formula 5 and of Formula 7 can be alkylated, acylated, converted into a urethane or carbonate derivative, phosphorylated, phosphonylated in reactions which per se are well known in the art, to yield compounds of Formula 1 where the R$_1$ group is other than hydrogen.

Reaction Scheme 1

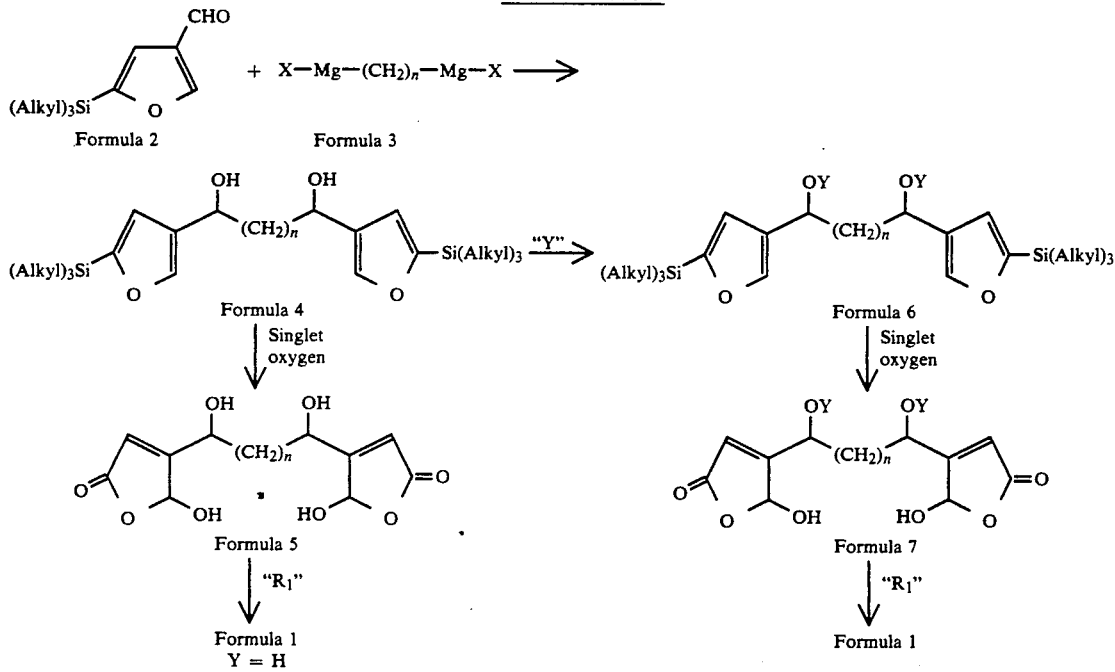

Alternatively, still in accordance with the present invention as shown on Reaction Scheme 1, the compounds of Formula 4 are reacted with a reagent which introduces the Y groups (as defined in connection with Formula 1) to the primary hydroxyl groups on the alpha carbons of the side chains in the 4 and 4'-positions of the furan nucleus. The reagent which introduces the Y group is symbolically shown in Reaction Scheme 1 as Y'. Depending on the nature of the Y group, Y' is an alkyl halide or other alkylating agent (to introduce an alkyl group), and acyl halide, acyl anhydride or other acylating agent (to introduce an acyl group), or an isocyanate to introduce a urethane function (when in Formula 1 Y is CONHR$_3$). Similarly, when in the compounds of the invention, as shown by Formula 1, Y is SO$_2$R$_3$ (sulfate) SO$_2$NHR$_3$ (sulfonamide) or Y is PO-(OH)$_2$, PO(OH)OR$_4$, PO(OH)R$_4$ PO(OR$_4$)$_2$ (phosphate and phosphonate), then the reagent Y' is an appropriate alkyl, aryl or arylalkyl sulphonyl chloride, alkyl, aryl or aryl amidosulfonylchloride, or an appropriate phosphonylchloride. When Y is CO—OR$_3$ (carbonate) then the Y group can be introduced by reaction with COCl$_2$ and an alcohol of the formula R$_3$OH.

The intermediate compounds of Formula 6 which have the desired Y substituent on the alpha hydroxyl groups of the side chains in the 4 and 4'-positions of the furane ring, are subjected to the action of singlet oxygen to obtain the bis-[5-hydroxy- 2(5H)-furanone-4-yl]-alkanes of Formula 7. As is described below in more

GENERAL EMBODIMENTS

Definitions

The terms "ester", "amine", "amide", "ether" and all other terms and terminology used here, (unless specifically defined in the present description) refer to and cover any compounds falling within the respective term as that term is classically used in organic chemistry.

Unless specifically noted otherwise, preferred esters are derived from the saturated aliphatic alcohols or acids of ten or fewer carbon atoms or from the cyclic or saturated aliphatic cyclic alcohols and acids of 5 to 10 carbon atoms. Particularly preferred aliphatic esters are those derived from lower alkyl acids or alcohols. Also preferred are the phenyl or lower alkylphenyl esters.

The term "alkyl" as used in the present description and claims includes straight chain alkyl groups, branched chain alkyl groups, cycloalkyl groups, alkyl substituted cycloalkyl groups, and cycloalkyl substituted alkyl groups. Unless the number of carbons is otherwise specified, "lower alkyl" means the former broad definition of "alkyl" groups but with the restriction that the group has 1 to 6 carbon atoms.

Unless specifically noted otherwise, the term "long chain alkyl" also means the former broad definition of "alkyl" groups but with the restriction that the group has no less than 4 carbon atoms, and no more than approximately 25 carbon atoms.

Unless specifically noted otherwise, preferred amides are the mono- and di-substituted amides derived from the saturated aliphatic radicals of ten or fewer carbon atoms, or the cyclic or saturated aliphatic-cyclic radicals of 5 to 10 carbon atoms.

Some of the compounds of the invention may contain a chiral center. Other compounds of the invention may contain more than one chiral center. Accordingly, the compounds of the invention may be prepared as mixtures of enantiomeric compounds (where the enatiomers may or may not be present in equal amounts) or as optically pure enantiomers. When there is more than one chiral center, the compounds of the invention may also be prepared as mixtures of diastereomers, or as pure diastereomers, and each diastereomer itself may be a mixture of enantiomers in 1:1, or other, ratios. Alternatively, each diastereomeric compound may be sterically and optically pure. However, all of the abovenoted forms, including optically pure enantiomers and mixtures thereof, as well as all diastereomers, are within scope of the present invention.

Some of the compounds of the invention may have cis and trans stereoisomers. The scope of the invention includes both pure stereoisomers as well as mixtures thereof.

A pharmaceutically acceptable salt may be prepared for any compound of this invention having a functionality capable of forming such salt, for example an acid or an amine functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The preferred compounds of the present invention are, with reference to Formula 1 and with respect to the 5-position of the furanone moiety, those where the substituent is hydroxy ($R_1$ is H), acetoxy ($R_1$ is $COCH_3$), or where $R_1$ is $CONHR_2$ and $R_2$ is lower alkyl or phenyl, more preferably phenyl.

With reference to the length of the alkyl chain which connects the two 5-hydroxy-2(5H)-furanone rings of the compounds of the present invention, the alkyl chain may contain between approximately 10 to 16 carbons (n is an integer between 8 to 14); particularly preferred are the compounds where the chain has 12 or 14 carbons (n is 10 or 12).

With reference to the Y substituent, compounds are preferred in accordance with the present invention where Y is H, straight or branch chained lower alkanoyl having 1 to 6 carbons, and where Y is $CONHR_3$, particularly where $R_3$ is phenyl.

The most preferred compounds of the invention are listed below with reference to Formula 8,
Compound 1 n=12, $R_6=CH_3$, $R_7=H$;
Compound 2 n=10, $R_6=NH$—Ph, $R_7=H$;
Compound 3 n=12, $R_6=C(CH_3)_3$, $R_7=H$;
Compound 4 n=12, $R_6=C(CH_3)_3$, $R_7=CONH$—Ph;

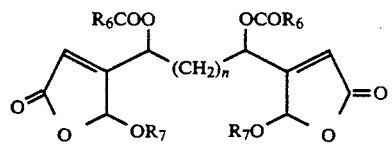

Formula 8

The compounds of the present invention are useful in pharmaceutical compositions to produce anti-inflammatory, immunosuppressant and anti-proliferative activity. The diseases, syndromes or conditions of mammals (including humans) which can be treated with pharmaceutical compositions containing one or more compounds of the invention (or salts thereof) include: inflammation, rheumatoid arthritis, osteoarthritis, rheumatic carditis, ocular and dermal inflammatory diseases, autoimmune diseases such as allergic diseases, bronchial asthma and myasthenia gravis, unwanted immune responses and unwanted proliferation of cells, psoriasis, acne, atopic diseases and allergic conjunctivitis.

The activity of the compounds of this invention is demonstrated by inhibition of the enzyme phospholipase $A_2$ in vitro and by reduction of inflammation in the mouse ear anti-inflammatory assay in vivo.

Activity of compounds of this invention may also be demonstrated by inhibition of phosphoinositide-specific phospholipase C. This activity has been reported for manoalide and may indicate anti-inflammatory utility. Bennett et al, *Molecular Pharmacology* 32:587-593 (1987).

Activity of the compounds may also be demonstrated by inhibition of ornithine decarboxylase, a rate limiting enzyme in cellular growth, which indicates use in treating psoriasis and neoplasis.

The compounds also modify calcium homeostasis. This activity is shown by effect on intracellular calcium levels in experiments using gastric glands, spleen cells, epithelial cells, $GH_3$ cells, etc. Calcium is inhibited from entering through the plasma membrane calcium channels and calcium release from intracellular stores is also blocked. Modification of calcium homeostasis is expected to have application in diseases of the nervous system involving modification of membrane lipids or transmitter release (Parkinson's, Alzheimer's), diseases of the cardiovascular system involving application of cardiac or vascular smooth muscle contractility and platelet aggregation (hypertension, cardiac infarction and atherosclerosis), diseases of the gastrointestinal tract such as ulcer disease, diarrhea, motility due to secretion of acid or $Cl^-$, diseases of the kidney involving renal handling of fluid and electrolytes (metabolic acidosis, alkalosis), and disease of abnormal growth (neoplasia, psoriasis).

The compounds of this invention have activity which is similar to that of manoalide, that is the compounds appear to be devoid of the endocrine properties of the glucocorticoids while having anti-inflammatory and immunosuppressive properties.

In the methods of this invention, the compounds of the invention are administered to mammals, including humans, in an effective amount to produce the desired activity, preferably in an amount of about 0.05 to 100 mg per day per kilogram of body weight. The amount of the compound depends upon the disease or condition being treated, the severity thereof, the route of administration and the nature of the host. The compounds may be administered topically, orally, parenterally or by other standard routes of administration.

Pharmaceutical compositions of this invention comprise compounds of Formula 1, and pharmaceutical carriers suitable for the route of administration. Standard methods for formulating pharmaceutical compositions of this type may be found in *Remington's Pharmaceutical Sciences*, Mack Publishing Company, Easton, Pa.

For topical administration, the pharmaceutical composition may be in the form of a salve, cream, ointment, spray, powder or the like. Standard pharmaceutical carriers for such compositions may be used. Preferably, compositions for topical administration will contain 0.05-5% of the active ingredient.

A typical cream formulation may contain the following:

| Ingredient | Parts by Weight |
| --- | --- |
| Water/glycol mixture (15% or more glycol) | 50-99 |
| Fatty alcohol | 1-20 |
| Non-ionic surfactant | 0-10 |
| Mineral oil | 0-10 |
| Typical pharmaceutical adjuvants | 0-5 |
| Active ingredient | 0.05-5 |

| Ingredients | Parts by Weight |
| --- | --- |
| White petrolatum | 40-94 |
| Mineral oil | 5-20 |
| Glycol solvent | 1-15 |
| Surfactant | 0-10 |
| Stabilizer | 0-10 |
| Active ingredient | 0.05-5 |

For oral administration, suitable pharmaceutical carriers include mannitol, lactose, starch, magnesium stearate, talcum, glucose and magnesium carbonate. Oral compositions may be in the form of tablets, capsules, powders, solutions, suspensions, sustained release formulations, and the like.

A typical tablet or capsule may contain the following:

| Ingredients | Percent w/w |
| --- | --- |
| Lactose, spray-dried | 40-99 |
| Magnesium stearate | 1-2 |
| Cornstarch | 10-20 |
| Active ingredient | 0.001-20 |

Parenteral compositions are prepared in conventional suspension or solution forms, as emulsions or as solid forms for reconstruction. Suitable carriers are water, saline, dextrose, Hank's solution, Ringer's solution, glycerol, and the like. Parenteral administration is usually by injection which may be subcutaneous, intramuscular or intravenous.

The compounds of this invention may be combined with other known anti-inflammatory/immunosuppressive agents such as steroids or non-steroidal anti-inflammatory agents (NSAID) in the pharmaceutical compositions and methods described herein.

The assay procedures by which useful biological activity of the compounds of the invention can be demonstrated, are described below.

Calcium Channel (Mobilization) Inhibition Assay

Polymorphonuclear leukocytes (PMNa), gastric glands, $GH_3$ cells, A431 cells, spleen cells, human keratinocytes corneal cells, etc. were loaded with the $Ca^{2+}$ sensitive fluorescent dye, Fura-2. The appropriate cell type was chosen and the potency and efficacy of the anti-inflammatory furanones on calcium mobilization, calcium channel inhibition was quantitated. The methods used for A431 cells listed below are representative of those used for other cells.

A431 cells were detached using a 5-10 min trypsin-EDTA treatment whereas $GH_3$ cells were treated 2 to 5 min with a 1% pancreatin solution. Cells were immediately washed twice in a 20 mM HEPES buffer (pH 7.4) containing 120 mM NaCl, 6 mM KCl, 1 mM $MgSO_4$, 1 mg/ml glucose and 1 mg/ml pyruvate and 1.4 mM calcium (medium A). Approximately $5 \times 10^6$ cells were suspended in medium A and incubated with 4 uM fura-2-AM for 15 min at 37° C.

After washing the fura-2 loaded cells, the uptake of dye was checked using fluorescence microscopy and found to be evenly distributed in the cytosol of all cells. Fluorescence was continuously recorded with a Perkin-Elmer LS-5 spectrofluorometer. The excitation wavelength was set at 340 nm and emission wavelength set at 500 nm. The cell suspension was continually stirred, maintained at 37° C. and equilibrated for approximately 5 min before addition of various agents. $[Ca^{2+}i$ was calculated using the following formula:

$$[Ca^{2+}]_i = 220 \times \frac{F - F_{min}}{F_{max} - F}$$

All fluorescence values were measured relative to a EGTA-quenched signal determined as follows: F was the relative fluorescence measurement of the sample. $F_{max}$ was determined by lysing the cells with digitonin (100 ug/ml) in DMSO. After $F_{max}$ was determined the pH was adjusted to 8, with NaOH and $Ca^{2+}$ chelated with 3 mM EGTA to totally quench the fura-2 signal and obtain $F_{min}$.

When quin-2- was used, cells were incubated with 10 uM quin-2- at 37° C. for 1 hour, washed and then used.

Mouse Ear Anti-Inflammatory Assay

Test compound and phorbol myristate acetate (PMA) are topically applied simultaneously to the pinnae of the left ears of mice. PMA alone is applied to the right ear. Three hours and 20 minutes after application, the mice are sacrificed, left and right ears removed, and standard sized bores taken. Edema (inflammation) is measured as the difference in weight between left and right ears [Van Arman, C. G., *Clin Pharmacol Ther* (1974) 16:900-904].

Inhibition of Phospholipase $A_2$

The effect of compounds of this invention on bee venom phospholipase $A_2$ is determined by the following procedure:

a. Bee venom phospholipase $A_2$ in 10 uM HEPES (pH 7.4) with 1 mM $CaCl_2$ is incubated with vehicle or test agent for 1.0 hour at 41°.
b. 1.36 mM phosphotidylcholine, 2 76 mM Triton X-100 are dispersed in buffer by sonication and then mixed with L-3 phosphotidylcholine, 1-palmitoyl-2-(1-$^{14}$C) palmitoyl for 10 min.
c. Start the reaction by the addition of enzyme (0.495 units/ml).
d. Incubation for 15 sec. at 41°.
e. Reaction is terminated by addition of 2.5 ml of isopropanol: n-heptane: 0.5M $H_2SO_4$ (40:10:1; v:v:v:).
f. 2.0 ml n-heptane and 1.0 ml $H_2O$ added; mixture centrifuged.
g. 2.0 ml n-heptane removed and treated with 200-300 mg of silica gel HR60.
h. Samples centrifuged; 1 ml of n-heptane SN removed and added to 10 ml scintillation fluid.
i. Samples counted on a scintillation counter.

Inhibition of Phosphoinositide-specific Phospholipase C

The effect of compounds of this invention on phosphoinositide-specific phospholipase C may be determined by procedures described by Bennett et al, *Molecular Pharmacology* 32:587-593 (1987).

Activity Data

In the above-described phospholipase $A_2$ assay the compounds of the invention were found to provide 50% inhibition ($IC_{50}$) of bee venom phospholipase $A_2$ at the following concentrations (in micromoles), as indicated in Table 1.

TABLE 1

| Phospholipase $A_2$ Assay. | |
| --- | --- |
| Compound name or number | $IC_{50}$ (um) |
| 1 | 0.01 |
| 2 | 0.03 |
| 3 | 0.02 |
| 4 | >1 |
| manoalide* | 0.03 |

*Data for monoalide are provided for comparison.

SPECIFIC EMBODIMENTS

The compounds of the present invention can be made by the synthetic chemical pathways which were described above in general terms, and specifically illustrated in the specific examples below. The synthetic chemist will readily appreciate that the conditions described here in general terms, and specifically, can be generalized to any and all compounds represented by Formula 1. Furthermore, the synthetic chemist will readily appreciate that the herein described synthetic steps may be varied or adjusted by those skilled in the art without departing from the scope and spirit of the invention.

With regard to the reaction step of exposing the bis-(2-trialkylsilyl-4-furyl)-alkane intermediate compounds (compounds of the Formula 4 and 6) to the action of singlet oxygen, the following is noted.

The conditions of these reactions are described in detail in connection with several specific examples. In general terms, the reactions are preferably conducted in a mixture of water and acetone or in a mixture of water and tetrahydrofuran, and in some instances in substantially neat tetrahydrofuran, in the presence of an initiator, preferably Rose Bengal dye (preferably polymer bounded), which is added to the reaction mixture. The reaction mixture and vessel is flushed with oxygen and the reaction is conducted at low temperature, at approximately −78° C., or for the herein described reactions preferably at approximately 0° C., under a constant positive pressure of oxygen for a number of hours, typically 1 to 7 hours. The mixture is typically irradiated with a 150 Watt flood lamp. Work-up of the reaction mixture after irradiation usually includes concentration by evaporation of the solvent, followed by chromatography on silica gel, in columns or on preparative silica plates.

The following examples of specific compounds of the invention, and specific examples of the synthetic steps in which the compounds and certain intermediates are made, are set out to illustrate the invention, not to limit its scope.

2-Trimethylsilyl-4-furaldehyde (Compound 5)

n-Butyl lithium (a 2.5M solution in hexane; 28.8 ml, 72 mmol) was added to a solution of morpholine (6.28 ml, 72 mmol) in tetrahydrofuran (700 ml) at −78° under argon. After 20 minutes, 3-furaldehyde (7.0 g, 72 mmol) was added. After another 20 minutes, sec-butyl lithium (a 1.3M solution in cyclohexane; 55.4 ml, 72 mmol) was added dropwise and stirring continued at −78° for 7 hours before trimethylsilyl chloride (27 ml, 216 mmol) was added. Stirring was continued overnight (14 hours) while the cooling bath was allowed to attain room temperature. The solution was poured into ice cold 10% (v/v) hydrochloric acid (200 ml) and after stirring at 0° for 10 minutes, the layers were separated. The aqueous phase was extracted with diethyl ether. All the organic phases were combined, dried (magnesium sulfate) and evaporated to dryness to give a light brown oil, which was purified by flash chromatography on silica using 2% ethyl ether/hexane. Fractions with $R_f$ of about 0.30 (silica, 10% ethyl ether/hexane) on evaporation gave the title aldehyde as a light yellow oil, b.p. 48°-50°/0.25 torr.

$^1$H NMR (CDCl$_3$) 0.29 (s, 9H), 6.98 (s, 1H), 8.25 (s, 1H) and 9.95 (s, 1H).

$^{13}$C NMR (CDCl$_3$) −2.0, 116.2, 128.9, 155.3, 164.1 and 184.5.

HRMS exact mass calculated for $C_8H_{12}O_2Si(M^+)$ 168.0607, found 168.0588.

2-Triethylsilyl-4-furaldehyde (Compound 6)

n-Butyl lithium (a 2.5M solution in hexane: 30.6 ml, 76.5 mmol) was added to a solution of morpholine (6.66 ml, 76.5 mmol) in tetrahydrofuran (500 ml) at −78° under argon. After 15 minutes, 3-furaldehyde (6.3 ml, 72.8 mmol) was added. After another 20 minutes, sec-butyl lithium (a 1.3M solution in cyclo-hexane; 59.0 ml, 76.5 mmol) was added dropwise and stirring continued at −78° for about 2 hours before triethylsilylchloride (13.4 ml, 80.1 mmol) was added. Stirring was continued overnight (14 hours) while the cooling bath was allowed to attain room temperature. The solution was poured into ice cold 10% (v/v) hydrochloric acid (100 ml) and another stirring at 0° for 10 minutes, the layers were separated. The aqueous phase was extracted with diethyl ether. All the organic phases were combined, dried (magnesium sulfate) and evaporated down to give an oil, which was distilled under high vacuum to give the 5-triethylsilyl-3-furaldehyde as a pale yellow oil, boiling point 85°-90°/0.4 torr.

IR (neat) 1680 cm$^{-1}$ $^1$H NMR (CDCl$_3$) 0.79 (q, 6H, J=7.3 Hz), 0.90 (t, 9H, J=7.3 Hz), 7.0 (s, 1H), 8.26 (s, 1H) and 9.95 (s, 1H).

$^{13}$C NMR (CDCL$_3$) 2.9, 7.1, 117.2, 128.8, 155.6, 162.3 and 184.6.

HRMS m/e exact mass calculated for C$_{11}$H$_{18}$O$_2$-Si(M+) 210.1076, found 210.1071.

1.14-Diacetoxy-1,14-bis(2-Triethylsilyl-4-furyl)tetradecane (Compound 7)

2-Triethylsilyl-4-furaldehyde (Compound 6, 530 mg, 2.52 mmol) was added to a solution of 1,12-dodecylmagnesium bromide (1.26 mmol; prepared from 414 mg 1,12-dibromododecane and 77 mg of magnesium turnings) in THF (3 ml) at 0° C. under argon. When all the aldehyde was consumed, acetic anhydride (0.71 ml, 7.57 mmol) was added. After stirring at room temperature for 14 hours the mixture was quenched with water. Extraction (ethyl ether) and evaporation of the dried (magnesium sulfate) extracts gave an oil, which was purified by flash chromatography on silica using (10% ethyl ether/hexane to give the titled ester. IR (CHCl$_3$) 1725.

$^1$HNMR (CDCl$_3$) 0.76 (t, 12H, J=7.6 Hz), 0.98 (t, 18H, J= 7.6 Hz), 1.24 (br, 20H), 1.95 (m, 4H), 2.04 (s, 6H), 5.78 (t, 2H, J=7.3 Hz), 6.59 (s, 2H) and 7.60 (s, 2H).

$^{13}$C NMR (CDCl$_3$) 2.87, 6.94, 21.0, 25.2, 27.1, 29.0, 29.2, 29.3, 29.4, 32.7, 34.6, 63.3, 68.5, 119.8, 125.0, 144.7, 159.5 and 178.

HRMS exact mass calculated for C$_{38}$H$_{66}$O$_6$Si$_2$(M+), 674.4398, found 674.4389.

1,14-Diacetoxy-1,14-bis[5-hydroxy-2(5H)-4-furanoyl]-tetradecane (Compound 1)

A mixture of 1,14-diacetoxy-1,14-bis(2-triethylsilyl-4-furyl)tetradecane (Compound 7, 298 mg, 0.43 mmol) Rose Bengal (ca. 5 mg) and water (1 ml) in acetone (20 ml) was exposed to singlet oxygen at 0° C. for 4 hours. On evaporation, the residue was purified by a silica column using 60% ethyl acetate/hexane to give the desired furanone. IR(CHCl$_3$) 3400 and 1750-1850.

$^1$HNMR (CDCl$_3$) 1.25 (brs+m, 20H), 1.80 (m, 4H), 2.16 (s, 6H), 5.50 (brt, 2H), 5.70 (brs, 1H), 5.92 (brs, 2H) and 6.10 (br, 2H).

$^{13}$CNMR 21.0, 25.0, 29.2, 29.4, 29.6, 29.7, 33.1, 69.7, 69.9, 70.0, 98.6, 118.9, 119.0, 119.1, 119.3, 119.4, 167.7, 171.2 and 171.7.

LRMS m/e (% abundance) 510 (M+, 22) 468 (100), 451 (41), 408 (87), 391 (55), 390 (45), 364 (22) and 347 (19).

1,12-Di(N-phenylcarbamoyl)-1,12-bis(2-triethylsilyl-4-furyl)dodecane (Compound 8)

2-Triethylsilyl-4-furaldehyde (Compound 6, 100 mg, 0.5 mmol) was added to 1,10-dodecylmagnesium bromide (1.13 mmol; prepared from 339 mg, 1,10-dibromodecane and 61 mg magnesium turnings) in THF (1 ml) at 0° C. under argon. After the Grignard reagent was spent, phenyl isocyanate (0.26 ml, 2.38 mmol) was added. After stirring at room temperature for 14 hours, the mixture was quenched with water. Extraction (ethyl ether) and evaporation of the dried (magnesium sulfate) extracts gave an oil, which was purified by flash chromatography on silica using 10% ethyl acetate/hexane to give the titled carbamate.

IR (CHCl$_3$) 3440, 1735 and 1608.

$^1$H NMR (CDCl$_3$) (mixture of diasteromers) 0.75 (m, 12H), 0.95 (m, 18H), 1.25 (m, 16H), 1.85 (m, 4H), 5.80 (t, 2H, J=6.9 Hz), 6.32 (s, 1H), 6.65 (s, 1H), 6.8-7.65 (m, 10H), 7.61 (s, 1H) and 10.9 (br, 2H).

$^{13}$C NMR (CDCl$_3$) 2.78, 2.82, 6.93, 13.8, 22.4, 24.6, 25.2, 28.8, 29.0, 29.1, 29.2, 29.4, 31.3, 34.7, 69.5, 72.6, 118.7, 119.1, 119.7, 120.0, 123.3, 124.0, 124.1, 124.9, 128.3, 128.8, 129.0, 137.3, 138.0, 138.2, 144.2, 144.7, 151.7, 153.4, 155.6, 159.5 and 159.7.

LRMS (FAB) (m/e, % abundance) 823.43 [(M+Na)+, 0.1].

1,12-Di(N-phenylcarbamoyl)-1,12-bis[5-hydroxy-2(5H)-furano-4-yl] dodecane (Compound 2)

A mixture of 1,12-di(N-phenylcarbamoyl)-1,12-bis(2-triethylsilyl-4-furyl)dodecane (Compound 8, 250 mg. 0.31 mmol), Rose Bengal (ca. 3 mg) and water (1 ml) in tetrahydrofuran (40 ml) was exposed to singlet oxygen at 0° C. for 6 hours. On evaporation, the residue was purified by flash chromatography on silica using 60% ethyl acetate/hexane to give the titled furanone. IR (CHCl$_3$) 3420, 3300, 1760, 1730, 1600 and 1525.

$^1$HNMR (d$_6$-acetone) (mixture of diasteromers) 1.30 (m, 16H), 1.90 (m, 4H), 5.60 (br, 1H), 5.70 (br, 1H), 6.05, 6.45 (m, 4H), 7.00-7.65 (m, 10H), 8.9 (br, 2H).

$^{13}$C NMR (d$_6$-acetone) 25.3, 28.9, 29.2, 29.4, 29.7, 29.9, 30.0, 30.1, 30.2, 33.4, 70.2, 71.0, 98.4, 98.5, 98.9, 99.0 118.5, 119.4, 119.6, 120.5, 120.6, 124.0, 124.8, 129.4, 129.9, 130.0, 130.1, 138.7, 139.3, 140.1, 153.9, 169.1, 170.4, 170.8, 206.7 and 206.8.

HRMS exact mass calculated for C$_{34}$H$_{41}$N$_2$O$_{10}$ 637.2761, found 637.2748.

1,14-Di(tert-butanoyloxy)-1,14-bis(2-triethylsilyl-4-furyl)tetradecane (Compound 9)

2-Triethylsilyl-4-furaldehyde (Compound 6, 1.05 g, 4.97 mmol) was added to 1,12-dodecylmagnesium bromide (2.43 mmol; prepared from 0.79 g of 1,12-dibromododecane and 127 mg magnesium turnings) in THF (10 ml) at 0° C. under argon. When all the furaldehyde was consumed, 2,2-dimethylpropionyl chloride (0.69 ml, 5.58 mmol) was added. Stirring was continued at room temperature for 14 hours and the mixture was quenched with water. Extraction (ethyl ether) and evaporation of the dried (magnesium sulfate) extracts gave an oil, which was purified by flash chromatography on silica using 5% ethyl ether/hexane to give the titled ester.

IR(CHCl$_3$) 1725.

$^1$H NMR (CDCl$_3$) 0.75 (q, 12H, J=6.8 Hz). 0.97 (t, 18H, J =6.8 Hz), 1.24 (m, 20H), 1.80 (m, 4H), 5.76 (t, 2H, J=7.8 Hz), 6.55 (s, 2H) and 7.56 (s, 2H).

$^{13}$C NMR (CDCl$_3$) (CDCl$_3$) 3.14, 7.22, 25.3, 27.0, 29.2, 29.4, 29.5, 29.6, 34.9, 38.7, 68.4, 119.6, 125.2, 143.9, 158.9 and 177.8.

1,14-Di(tert-butanoyloxy)-1,14-bis[5-hydroxy-2(5H)-furano-4-yl]tetradecane (Compound 3)

A mixture of 1,14-di(tert-butanoyloxy)-1,14-bis(2-triethylsilyl-4-furyl)tetradecane (Compound 9, 990 mg, 1.31 mmol), Rose Bengal (5 mg) and water (1 ml) in acetone (70 ml) was exposed to singlet oxygen at 0° C. for 2 days. On evaporation, the residue was purified on a silica column using 40% ethyl acetate/hexane to give the desired furanone.

IR(CHCl$_3$) 3400 and 1730-1810.

$^1$H NMR (CDCl$_3$) 1.25 (m, 38H), 1.80 (m, 4H), 5.25 (br, 2H), 5.40 (brt, 2H), 5.91 (s, 2H) and 6.05 (br, 2H).

$^{13}$CNMR 24.6, 26.7, 26.8, 28.7, 28.8, 29.0, 29.1, 32.8, 38.7, 69.2, 98.1, 111.5, 118.3, 118.4, 167.8, 170.4, 178.5 and 178.6.

HRMS (FAB) exact mass calculated for $C_{32}H_{50}H_{10}N_a$ $(M+N_a)^+$ 617.3302, found 617.3289.

1,14-Di-(tert-butanoyloxy)-1,14-bis[5-(N-phenylcarbamoyl)-2(5H)-furano-4-yl]-tetradecane (Compound 4)

Phenyl isocyanate (0.10 ml, 0.93 mmol) was added to a mixture of 1,14-di(tert-butanoyloxy)-1,14-bis[5-hydroxy-2(5H)-furano-4-yl]-tetradecane (Compound 3 277 mg, 0.47 mmol) and copper (I) chloride (92 mg, 0.93 mmol) in N,N-dimethylformamide (3 ml) at 0° C. under argon. After 6 hours at 0° C., the mixture was quenched with water and extracted with ethyl acetate. The extracts were combined and washed successively with dilute HCl, saturated NaHCO$_3$ and brine. Evaporation of the dried (magnesium sulfate) organic phase gave an oil, which was purified by flash chromatography on silica using 30% ethyl acetate/hexane to give the titled furanone.

IR (CHCl$_3$) 3340, 1810, 1770 and 1735.

$^1$H NMR (CDCl$_3$), 1.30 (m, 38H), 1.80 (m, 4H), 5.65 (t, 2H, J=5.3 Hz), 6.04 (s, 2H), 6.99 (s, 2H) and 7.00-7.50 (m, 10H).

HRMS (FAB) exact mass calculated for $C_{46}H_{60}N_2O_{12}Na$ $(M+Na)^+$ 855.4044, found 855.4077.

What is claimed is:

1. A compound of the formula

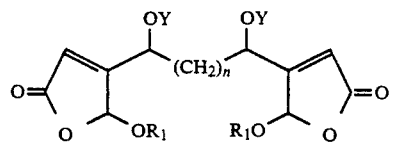

wherein

R$_1$ is H, alkyl of 1 to 20 carbons, CO—R$_2$, CO—O—R$_2$, CO—NH—R$_2$, or PO(OR$_2$)$_2$ or PO(OR$_2$)R$_2$, where R$_2$ independently is H, alkyl of 1 to 20 carbons, phenyl, or lower alkyl substituted phenyl or halogen substituted phenyl;

n is an integer between 8 to 14;

Y is H, alkyl having 1-20 carbon atoms, aryl(lower alkyl), aryl, lower alkyl(aryl), alkenyl containing one or more olephinic bonds and 1-20 carbon atoms, CO—R$_3$, CO—OR$_3$, CONHR$_3$, SO$_2$R$_3$, or SO$_2$NHR$_3$ where R$_3$ is aryl(lower alkyl), aryl, lower alkyl(aryl), alkenyl containing one or more olephinic bonds and 1-20 carbon atoms, further Y is PO(OH)$_2$, PO(OH)OR$_4$, PO(OH)R$_4$, or PO(OR$_4$)$_2$, where R$_4$ is independently alkyl of 1-20 carbons or phenyl, and pharmaceutically acceptable salts thereof.

2. A compound of claim 1 where R$_1$ is H, CO—R$_2$, or CO—NH—R$_2$.

3. A compound of claim 2 where R$_1$ is H.

4. A compound of claim 2 where R$_1$ is CO—NH—phenyl.

5. A compound of claim 1 where n is an integer between 10 and 12.

6. A compound of claim 5 where n is 10.

7. A compound of claim 5 where n is 12.

8. A compound of claim 1 where Y is H, CO—R$_3$, or CONHR$_3$, and R$_3$ is alkyl having 1 to 5 carbons, or is phenyl.

9. A compound of claim 8 where Y is CO—CH$_3$.

10. A compound of claim 8 where Y is CO—C(CH$_3$)$_3$.

11. A compound of claim 8 where Y is CO—NH—phenyl.

12. An anti-inflammatory pharmaceutical composition comprising a compound of claim 1 and a pharmaceutically acceptable excipient.

13. A compound of the formula

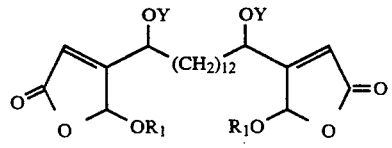

wherein

R$_1$ is H, CO—R$_2$ or CO—NH—R$_2$, where R$_2$ is straight or branched chain lower alkyl of 1 to 6 carbons, or R$_2$ is phenyl, and Y is H, CO—R$_3$, CONHR$_3$, where R$_3$ is straight or branched chain lower alkyl of 1 to 6 carbons, or R$_3$ is phenyl.

14. A compound of claim 13 where R$_1$ is H.

15. The compound of claim 14 where Y is CO—CH$_3$.

16. The compound of claim 14 where Y is CO—C(CH$_3$)$_3$.

17. The compound of claim 13 where Y is CO—C(CH$_3$)$_3$ and R$_1$ is CO—NH—Ph.

18. A compound of the formula

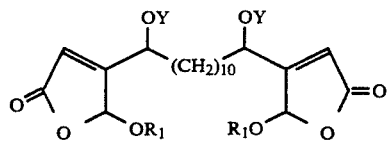

wherein

R$_1$ is H, CO—R$_2$ or CO—NH—R$_2$ where R$_2$ is straight or branched chain lower alkyl of 1 to 6 carbons, or R$_2$ is phenyl, and Y is H, CO—R$_3$, CONHR$_3$ where R$_3$ is straight or branched chain lower alkyl of 1 to 6 carbons, or R$_3$ is phenyl.

19. A compound of claim 18 wherein R$_1$ is H.

20. A compound of claim 18 wherein Y is CO—NH—phenyl.

21. The compound of claim 20 wherein R$_1$ is H.

* * * * *

UNITED STATES PATENT AND TRADEMARK OFFICE
CERTIFICATE OF CORRECTION

PATENT NO. : 5,225,571
DATED : July 6, 1993
INVENTOR(S) : Gary C.M. Lee

It is certified that error appears in the above-identified patent and that said Letters Patent is hereby corrected as shown below:

Column 7, line 36, add —A typical ointment formulation may contain the following:—

Column 8, line 22, "KCI" should be —KCl—;

Column 9, line 4, " 2 76" should be—2.76—;

Column 10, line 37, "$R_f$of" should be —$R_f$ of—;

Column 10, line 49, "hexane:" should be —hexane;—;

Column 12, line 27, "99.0 118.5," should be—99.0, 118.5,—;

Column 13, line 41, before "$PO(OR_2)_2$" delete —or—.

Signed and Sealed this

Fifth Day of April, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,225,571

DATED : July 6, 1993

INVENTOR(S) : Gary C. M. Lee

It is certified that error appears in the above-identified patent and that said Letters Patent is hereby corrected as shown below:

Column 3, line 2, after "chlorine" delete—.—.

Signed and Sealed this

Fifth Day of July, 1994

Attest:

BRUCE LEHMAN

Attesting Officer     Commissioner of Patents and Trademarks